United States Patent [19]

Hefele

[11] Patent Number: 4,862,900
[45] Date of Patent: Sep. 5, 1989

[54] ANKLE SUPPORT STRUCTURE

[76] Inventor: Wilhelm J. Hefele, Breitenbergstr. 3, D-8955 Airtrang, Fed. Rep. of Germany

[21] Appl. No.: 120,997

[22] Filed: Nov. 16, 1987

[30] Foreign Application Priority Data

Nov. 29, 1986 [DE] Fed. Rep. of Germany ....... 3640915

[51] Int. Cl.⁴ .............................................. A61F 5/04
[52] U.S. Cl. .................................. 128/80 H; 128/166
[58] Field of Search .................... 128/166, 80 C, 80 H

[56] References Cited

U.S. PATENT DOCUMENTS

| 1,624,266 | 4/1927 | Luder | 128/166 |
| 2,592,739 | 4/1952 | Richardson | 128/166 |
| 2,994,322 | 8/1961 | Cullen et al. | 128/80 H |
| 3,298,365 | 1/1967 | Lewis | 128/80 H |
| 3,515,136 | 6/1970 | Baker | 128/166 |
| 4,409,976 | 10/1983 | Pence | 128/80 H |
| 4,454,871 | 6/1984 | Mann et al. | 128/80 H |
| 4,590,932 | 5/1986 | Wilkerson | 128/80 H |
| 4,622,908 | 11/1986 | Tranberg | 128/80 C |
| 4,686,969 | 8/1987 | Scott | 128/80 C |
| 4,724,847 | 2/1988 | Nelson | 128/80 H |

FOREIGN PATENT DOCUMENTS 0210154  5/1987  European Pat. Off. .......... 128/80 C Primary Examiner—Edgar S. Burr
Assistant Examiner—Huong Q. Pham
Attorney, Agent, or Firm—Notaro & Michalos

[57] ABSTRACT

A U-shaped bow forming a bottom-sided yoke and side legs forms together with a curved front wall and upper rearwardly extending curved flaps an absolutely stiff shell for a patient's leg in order to hold the ankle absolutely immovable. The thin-walled ankle support structure replaces the usual cast and can already be used a short period after an operation of the ankle has been made.

7 Claims, 3 Drawing Sheets

ANKLE SUPPORT STRUCTURE

BACKGROUND OF THE INVENTION

The invention relates to an ankle support structure comprising a generally U-shaped bow consisting of a thin rigid material, the yoke of the U-shaped bow forming a bottom wall for the foot of a human and the pair of legs of the U-shaped bow contacting the calf of the human's leg at opposite sides thereof and extending upwards beyond the ankle.

An ankle support structure of this kind is known from DE-Patent Publication No. 34 35 955. The U-shaped bow is made of thermoplastic material and can be shaped to the contour of the human's leg by heat treatment. A binding tape must be wrapped around the vertical legs of the bow to fasten the support structure at the human's leg. This ankle support indeed can be used by individuals, particularly athletes have weak ankles to avoid injuries and by patients who, some weeks after an operation have removed the usual plaster cast. However, this support cannot replace such a cast immediately after an operation of the ankle, because the upstanding legs can move with respect to one another, and to the leg of a human i.e., the legs of the U-shaped bow can be bent and distorted.

U.S. Pat. No. 4,133,311 shows an ankle support structure made of cloth fabric layers comprising an inner, ankle enveloping layer of a resilient material and an outer, non-resilient but flexible layer secured to the outside surface of the inner layer. The inner layer can be snugly wrapped completely around the upper part of the ankle and secured there. Straps are provided to be wrapped around the foot and fastened at the sides of structure to form a stirrup-like support. While this proposal can be used in the same case as the known structure mentioned at the beginning also the drawbacks are the same.

OBJECTS OF THE INVENTION

It is, therefore, a primary object of this invention to provide an improved support structure for a human ankle.

Another object of this invention is to provide an orthosis or ankle support structure which can be used after an operation of the ankle instead of a plaster and which provides that the ankle is held absolutely stationary within the support.

Another object of this invention is to provide an ankle support structure of the type described that provides an inflexible, dimensionally stable thin shell snugly surrounding the contour of the leg of a human.

Still another object of this invention is to provide an ankle support structure of the type described that provides a generally U-shaped bow, the upstanding legs thereof rigidly connected with one another by an integral front wall leaving a front opening for the foot of a human above the yoke of the bow.

Another object of the invention is to provide an ankle support structure of the kind described that provides a rigid thin-walled shell having a front opening, an upper calf opening and a rearward heel opening, whereby non-resilient but somewhat flexible flaps of the shell between the calf and heel openings provide a rearward access for the human's leg.

SUMMARY OF THE INVENTION

Briefly, an orthosis or ankle support structure comprises a generally U-shaped bow and a rigid front wall connecting upper sections of said pair of legs of the U-shaped bow above a front opening for the human's foot, said front wall and the U-shaped bow thus forming an integral, one-piece inflexible shell, a pair of rearwardly extending, inwardly bent flaps associated with the upper sections of said pair of legs respectively, the ends of the flaps at least nearly contacting one another in the region of the Achilles' tendon and at least the ends of the flaps having a sufficient flexibility to widen the flaps for inserting the human's leg, and closure means connecting said flaps with one another.

Thanks to the rigid integral front wall a non-deformable thin-walled shell is provided snugly enclosing the human foot, leaving only three openings adapted to the contours of the foot front, calf and heel of the human. The shin-bone is firmly held in contact with the rigid front wall of the support structure, the upstanding legs forming side walls of the shell provide for a side support of the human's leg and the flaps serve to avoid a rearward movement thereof, thereby excluding that the ankle is subjected to any movements.

The novel ankle support structure provides for a fixation of the ankle in the same way as a cast without having the disadvantages thereof. The patient can take a shower, bath and swim and also can use his or her usual shoes.

In a preferred embodiment of the invention the yoke of the bow is rearwardly extended to form a heel supporting wall.

Further it is preferably provided that the legs of the bow are increasingly broadened rearwardly beginning at the ankle region and ending at the heel supporting wall thus forming heel side support gussets. Thereby any movements of the heel are prevented.

According to a further embodiment of the invention the rearward edges of the flaps contact one another along the Achilles' tendon. Thereby the flaps mutually support one another and the closure means has only the effect to secure the flaps in place. The closure means can be in form of a pair of strips commercially available under the trademark VELCRO, one thereof fastened at the outer surface of one leg of the U-shaped bow and overlapping both flaps and the other one fastened at the opposite bow leg. Also hook and loop fastening means can be used.

In a further preferred embodiment of the invention it is provided that the material of the ankle support structure comprises two layers, each consisting of a plurality of perlon textile plys and an intermediate stiffening layer consisting of one of the items comprising carbon fibers and glass fibers and wherein the three layers are laminated together by a casting resin. This construction results in a thin but absolutely rigid and dimensionally stable shell.

DETAILED DESCRIPTION OF A PREFERRED EMBODIMENT

Figure 1:
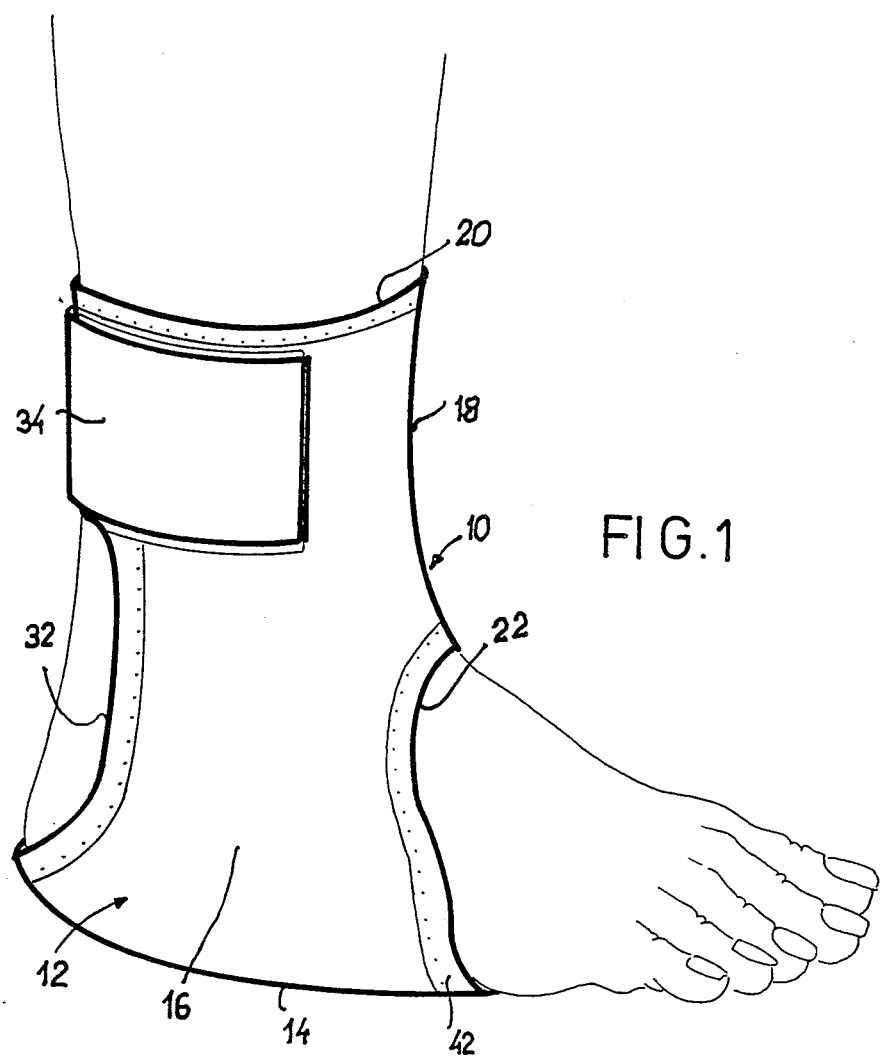
FIG. 1 is a perspective view of an ankle support structure in use.

An ankle support structure or orthosis 10 comprises a bow 12 having a generally U-shaped cross-section. The bow 12 consists of a yoke 14, which forms a central bottom panel, and a pair of substantially parallel legs 16 which extend upwards from the yoke 14 and form side panels. The upper areas of the legs 16 are connected with one another in a one-piece fashion by a curved front wall 18. The yoke 14, the legs 16 and the front wall 18 form a seamless one-piece shell of high stiffness. The legs 16 and the front wall 18 extend upwards beyond the ankle and end in the calf region.

A pair of curved flaps 24 are associated with the upper sections of the legs 16. In the position of use of the support structure 10 the flaps 24 contact one another with their vertical end edges 26 along the Achilles' tendon. Thus, the curved front wall 18, the pair of curved legs 16 and the pair of curved flaps 24 form a closed oval ring snugly enclosing the calf of a human's leg and bordering a calf opening 20. The front wall 18 extends down to a front opening 22 which is further bordered by the legs 16 and the yoke 14.

The yoke 14 projects rearwardly with respect to the rearward edges of the legs 16 as measured below the flaps 24. The yoke projection forms a heel supporting bottom wall 28. Both legs 16 are also increasingly broadened rearwardly in downward direction, thus forming gussets 30 which serve as side support walls for the heel. Both rearward edges of the legs 16, the lower edges of the flaps 24 and the heel supporting bottom wall 28 border a rearward heel opening 32.

The flaps 24, though integrally formed with the bow 12, are of somewhat lower stiffness than the rest of the shell. The flaps 24 are of such very flexibility, that they can be widened to form an insert channel for the human's leg and after having inserted the leg they spring back into their original closing positions mutually contacting one another and enclosing the calf. A closure device 34 in form of a pair of strips available on the market under the trademark VELCRO serves to hold the flaps 24 in place.

Figure 2:
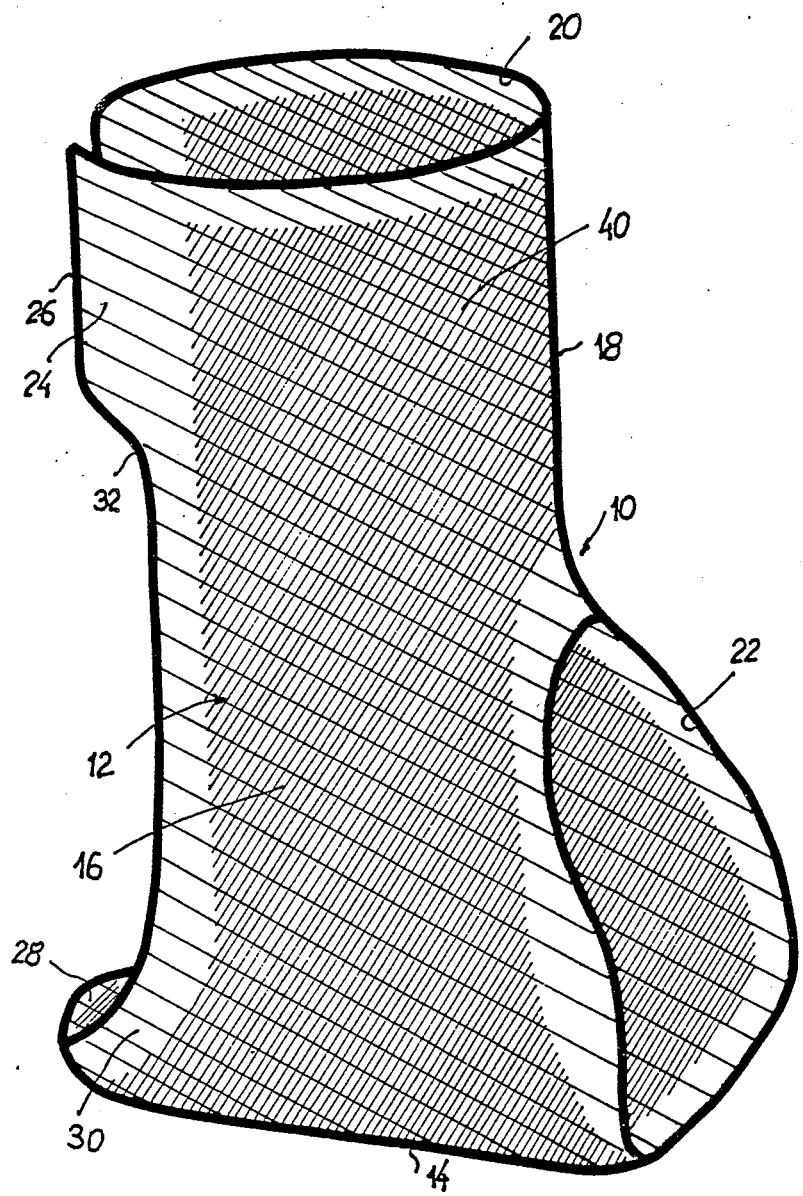
FIG. 2 is a perspective view of the ankle support structure of FIG. 1, with the closure means omitted, however, showing areas of reinforcement of the material.
Figure 3:
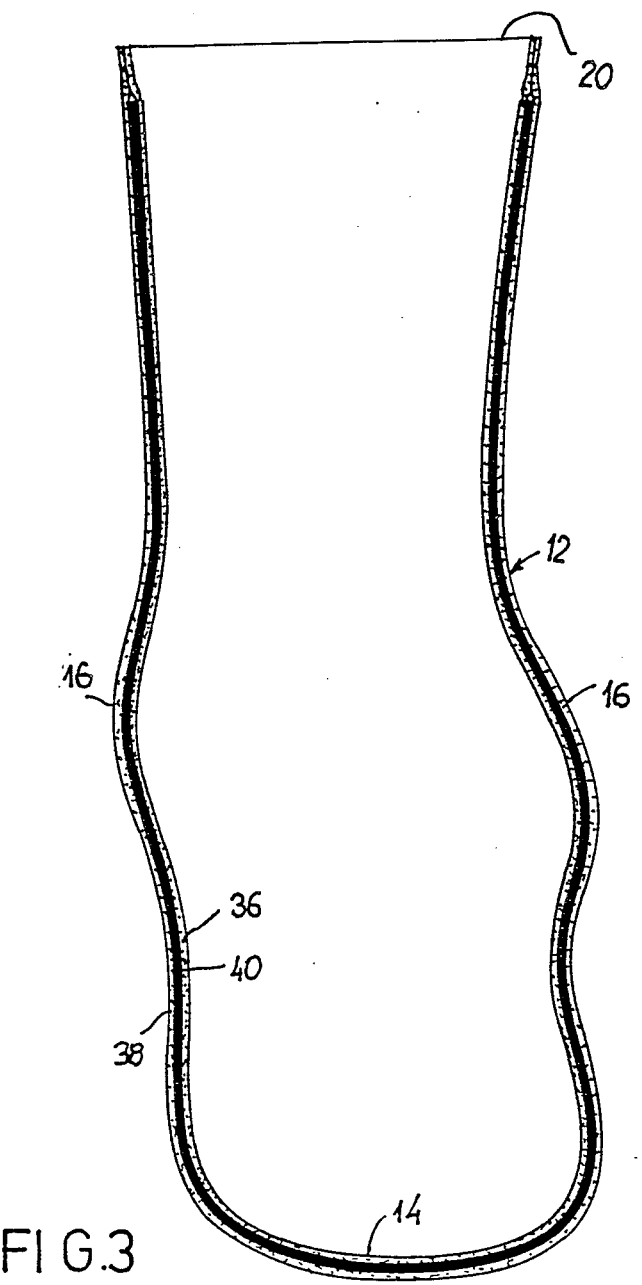
FIG. 3 is a vertical cross-sectional view of the ankle support structure.

The ankle support structure 10 consists of a multilayer material. An inner layer 36 and an outer layer 38 consist of a multiply perlon fabric respectively. A reinforcement layer 40 consisting of a carbon fibre mat forms an intermediate layer. The three layers are sandwiched together and connected by a polyacrylic resin. The reinforcement layer 40 extends over the main areas of the yoke 14, the legs 16 and the front wall 18. In FIG. 2 the reinforcement areas are shown by cross-hatching. The reinforcement layer 40 is omitted in the areas of the flaps 24 and along the edges bordering the front opening 22, the calf opening 20 and the heel opening 32. In the region of the reinforcement layer 40 the support structure is absolutely rigid and therefore dimensionally stable while the remaining areas not covered by the reinforcement layer are somewhat flexible, so that they can adapt to the contours of the human's leg.

A cushion layer can be provided at the inner surface of the inner layer 36 particularly in the region of the front wall 18 and in the region of the ankle in both legs 16. The whole inside surface of the support structure 10 is covered with a watertight inner lining 42 which is drawn out of the three openings 20, 22, 32 and folded back on the outer edge surfaces and is then stitched on, as shown in FIG. 1.

In conclusion, the bow 12, the front wall 18 and the flaps 24 form a one-piece seamless thin-walled shell which in the area of the reinforcement layer is of highest possible stiffness. Thanks to the concept that the somewhat flexible flaps 24 are in a mutual supporting contact with one another at the rearward edges 26 the calf of the patient is completely enclosed and the leg of the patient in the area of the ankle is held absolutely immovable. The closure device 34 is not subjected to any stresses but serves only to secure the flaps 24 in place.

A combined method of laminating and pouring the walls of the supporting structure 10 allows a precise adaption to the contour of the patient's leg by use of a model of plaster produced before.

I claim:

1. An ankle support orthosis comprising:
   a bow (12) which is U-shaped in vertical cross-section and which has a bottom yoke panel (14) with opposite side edges, a front edge and a rear edge and being for contacting the bottom of a human foot, and a pair of side leg panels (16) connected as one piece to and extending upwardly from the opposite side edges of said bottom yoke panel for contacting a human ankle and calf, each side leg panel having upper and lower front edges, upper and lower rear edges and upper edges;
   a curved front wall (18) having an upper edge and being connected as one piece between the upper front edges of said side leg panels and defining with the lower front edges of said side leg panels, and the front edge of said bottom yoke panel, a front opening (22) for a human foot, said curved front wall and said leg panels together forming an integral step-free relatively rigid shell portion of high stiffness so as to hold an ankle absolutely immovable, said shell portion having a substantially U-shaped horizontal cross-section;
   said bottom yoke panel, said side leg panels and said curved front wall, together forming a relatively rigid, integral, one-piece shell which is undetachably closed above said front opening;
   a pair of rearwardly extending, inwardly curved flaps (24) connected to respective upper rear edges of said side leg panels, said curves flaps having rear end edges (26) which are adjacent one another for covering the region of a human Achilles' tendon, at least one of said curved flaps being relatively flexible as compared to said shell, for permitting the spreading apart of said rear end edges for insertion of a human leg, and said curved flaps having upper edges; and
   closure means connected between said curved flaps for retaining said shell on a human leg;
   the upper edges of said front wall and side leg panels defining an upper calf opening and the lower rear edges of said side leg panels and the rear edge of said bottom yoke panel defining a rearward heel opening of the shell.

2. An ankle support orthosis as claimed in claim 1, wherein the yoke panel is rearwardly extended to form a heel supporting bottom wall.

3. An ankle support orthosis as claimed in claim 2, wherein each of said side leg panels widens rearwardly in the region of said heel supporting bottom wall to form gussets.

4. An ankle support orthosis as claimed in claim 1, wherein the material of said shell comprises at least one layer made of a plurality of perlon textile plies and a stiffening layer made of one of carbon fibers and glass fibers, and wherein the layers are laminated together by a casting resin.

5. An ankle support orthosis as claimed in claim 4, wherein the stiffening layer is omitted in the flaps and in edge regions surrounding the front opening, the upper calf opening and the rearward heel opening of the shell.

6. An ankle support orthosis as claimed in claim 1, wherein at least the shell consisting of said U-shaped bow and said front wall is formed anatomically corresponding to a human leg.

7. An ankle support orthosis as claimed in claim 1, wherein the rear end edges of the flaps contact one another along the Achilles' tendon.

* * * * *